(12) United States Patent
Mueller et al.

(10) Patent No.: US 7,090,801 B2
(45) Date of Patent: Aug. 15, 2006

(54) MONITORING DEVICE FOR MELTING FURNACES

(75) Inventors: Hilmar R. Mueller, Bellenberg (DE); Horst Thiess, Neu-Ulm (DE)

(73) Assignee: Wieland-Werke AG, Ulm (DE)

( * ) Notice: Subject to any disclaimer, the term of this patent is extended or adjusted under 35 U.S.C. 154(b) by 129 days.

(21) Appl. No.: 10/642,388

(22) Filed: Aug. 15, 2003

(65) Prior Publication Data
US 2004/0114663 A1    Jun. 17, 2004

(30) Foreign Application Priority Data
Aug. 16, 2002  (DE) ................. 102 37 603

(51) Int. Cl.
*C21D 11/00*   (2006.01)
*C21B 7/24*    (2006.01)
(52) U.S. Cl. ................. 266/78; 266/99; 432/157
(58) Field of Classification Search .......... 266/78, 266/99; 373/145, 155; 432/157
See application file for complete search history.

(56) References Cited
U.S. PATENT DOCUMENTS 2,990,542  A * 6/1961 Seitz ................. 373/145
4,367,866  A    1/1983 Acker et al.
5,319,671  A * 6/1994 Hopf ................ 373/145
5,479,437  A * 12/1995 Hayashi ............. 373/150

FOREIGN PATENT DOCUMENTS

DE   41 20 205      12/1992
DE   196 02 249     7/1997

OTHER PUBLICATIONS

REFRACTECH Advertisement, www.refractech.com.au/saveway.htm, Mar. 2005.*
Überwachung des Futterverschleißes von Tiegelund Rinnenöfen, Hopf, Giesserei 89 (Jan. 15, 2002), pp. 36-42.

* cited by examiner

*Primary Examiner*—Scott Kastler
(74) *Attorney, Agent, or Firm*—Flynn, Thiel, Boutell & Tanis, P.C.

(57) ABSTRACT

Cracking of a crucible can cause heavy damage to the system in melting furnaces. A reliable monitoring of threatening breaking out of the melt is therefore needed. For this purpose a monitoring device for melting furnaces is provided to monitor the breaking out of melt and includes a closed circuit consisting of several conductor sections with at least a partially conducting surface and a measuring/displaying device. A first conductor section is series connected through an ohmic resistor R to a second conductor section. The first conductor section is arranged directly adjacent, however, electrically isolatingly spaced from and with respect to the second conductor section.

19 Claims, 3 Drawing Sheets

MONITORING DEVICE FOR MELTING FURNACES

FIELD OF THE INVENTION

The invention relates to a monitoring device for melting furnaces to monitor the breaking out of melt, in particular for coreless or channel-type induction furnaces, including a closed circuit consisting of several conductor sections with at least a partially conducting surface and a measuring/ indicating device.

BACKGROUND OF THE INVENTION

The cracking of a crucible can cause heavy damage to the system in induction furnaces, and in addition can endanger personnel. Various systems are already being used for the timely supply of information regarding threatening breaking out of melt.

Usually in the simplest case the contact of melt with the coil is indicated through ground fault. Warning systems installed in front of the coil, for example on an electrically insulating refractory liner applied to the coil, create a warning prior to the running out melt contacting the coil. The control and design of the warning systems exist in various forms. Simple systems measure the resistance in the circuit crucible—warning system—gauge. For this purpose the gauge has to be connected by means of a contact, in most cases a stainless steel flag embedded into the bottom refractory, to the crucible surrounded by the induction coil. When the crucible cracks, a melt tongue run out penetrates the refractory liner and contacts the warning system. The prior very large electrical resistance of the refractory liner decreases, due to the contact, practically to zero. The monitoring system indicates this optically or acoustically and switches the furnace off.

The disadvantage of this system is that when the contact in the circuit is lost a change is not displayed, for example, due to a cable disruption caused by shrinkage of the crucible or due to oxidation of the stainless steel flag, which results in an increase of the transfer resistance at the flag. This results in the monitoring device becoming ineffective since the resistance display remains at infinite even when a melt tongue touches the warning system.

Attempts to guarantee an earlier recognition of a crack in the crucible with the breaking out of melt are known from the publication of Hopf, Giesserei 89 (2002), No. 1, Pages 36–42. The residual wall thickness is thereby measured by the temperature based on the temperature dependency of the specific electric resistance of refractory material, and is utilized to evaluate the localized wear of the furnace wall thickness. Sensors are for this purpose installed in a refractory construction, which sensors are made of two wire-shaped, comb-like electrodes which are embedded into a flexible mica or ceramic material. If the temperature now increases at one point of the sensor, then the specific electric resistance of the ceramic is reduced at this point. This resistance change between the two electrodes is detected by a measuring device and is evaluated.

However, this works only to a limited degree in particular in furnaces with electric or clay-graphite crucibles since the explicit temperature dependency of the resistance does not exist here.

SUMMARY OF THE INVENTION

The basic purpose of the invention is to provide a monitoring device for melting furnaces which monitors a break out of melt with greater reliability.

The purpose is attained by a monitoring device for melting furnaces to monitor the break out of melt including a closed circuit consisting of several conductor sections with at least a partially conducting surface and a measuring/ displaying device, wherein a first conductor section is series connected to an ohmic resistance R with a second conductor section, and the first conductor section is arranged directly adjacent, however, electrically isolatingly spaced from and with respect to the second conductor section.

The invention is thereby based on the premise that the melt breaking out through a crack in the pot should be recognized early. In particular in the case of induction furnaces the early recognition should have the result that the escaping melt tongue does not contact the coil. The invention is furthermore also suited for use in electric or clay-graphite crucibles, thus in devices which have not a distinct dependency on the temperature of the resistance. In addition, the invention is to recognize breakdowns in monitoring during operating conditions.

The monitoring device includes for this purpose an ohmic resistor R configured from series connected conductor sections. The ohmic resistor is positioned when in use at a point on the furnace where it is not directly subjected to high temperature. The influence of the temperature may neither damage the resistor nor may it substantially change the electric resistance. The first conductor section extends directly adjacent to the second conductor section along the monitoring zone on the melting furnace. The spacing between the two conductors is as small as possible so that breaking out melt directly short-circuits both conductor sections by short circuiting the resistor R. The surfaces of the conductor sections are for this purpose at least partially electrically conductive. Other areas of the conductor sections, for example supply lines, can also be isolated on the surface. The respective conductor section is thus in general understood to be the electric conductor extending before or after the ohmic resistor R.

For a particular freedom in the design of the arrangement, the conductor sections are designed such that the area of the furnace to be monitored is focal point covered, line-like or flat with the monitoring device. The conductor sections are for this purpose advantageously of a comb-like design, both comb structures being interleaved with one another. The conductor sections are alternatively or additionally of a meandering design and loop around one another.

In principle it is possible to essentially freely choose the magnitude of the ohmic resistor R. The ohmic resistor R is advantageously larger by a factor of 100 to 1000 than the resistance value of the conductor sections connected in series. Further criteria for selecting the resistor result, for example, from the use of refractory liner arranged on the conductor sections of the furnace. The electric resistance value of spacers and fixtures must thereby also be considered. When the conductor sections are spaced a small distance from one another, the conductor sections must still be sufficiently electrically isolated from one another for a reliable operation of the monitoring device. An ohmic resistor value of R=0.5 to 50 kohms, in particular 1 to 5 kohms, is a preferred embodiment.

Part of a reliable monitoring of a breaking out of melt also involves recognizing that breakdowns of the monitoring device have occurred and can be quickly eliminated. A breakdown in the operation of a furnace must be recognized at one glance by the personnel. The measuring/displaying device shows, for this purpose during the undisturbed normal operation essentially, the magnitude of the ohmic resistor R. The indication is okay when the defined resistance of, for example, 2 kohms is indicated, which means no break in the cable or no other breakdown exists. Essentially it means in the case of the undisturbed normal operation that due to the series connection, except for R, the resistor parts of the respective conductor sections are added which, however, due to their small value play only a subordinate role. Upon a breakdown due to a conductor break, the measuring/displaying device indicates the resistance value as "infinite". The monitoring device with supply lines is checked for function through this self-diagnostic function. A breakdown in the circuit does not yet mean a direct danger. The cause of the breakdown can be determined and eliminated. When the melt tongue contacts during the breaking out of melt, for example, two prongs of the warning-system comb and short-circuits the conductor sections, the resistance value drops to "zero". This is in the automated condition causes a turning off of the furnace. Since an especially high danger begins with an unexpected breaking out of melt, an automation feature offers the greatest amount of safety by preventing further endangerment of personnel in the area of the furnace. The resistance indications "infinite" or "zero" are advantageously each coupled additionally with an acoustic or optic display.

Monitoring of some areas of a melting furnace are of particular interest. The conductor sections are principally guided around the crucible filled with melt. The conductor sections are in a preferred embodiment arranged holohedrally on the circumference of the crucible filled with melt. Some areas, for example the neck area, inductor or flange-mounted area of a channel-type furnace or the coil area in a coreless-type induction furnace, is, if applicable covered by a particularly dense net of conductor sections.

Through the operation for many weeks under the effects of heat, a monitoring device must be permanently mounted on the furnace. This occurs advantageously on the surface of a refractory liner, which surface faces away from the crucible filled with melt. This surface must be configured to have a magnitude of electric resistance corresponding to the ohmic resistor R. The refractory liner in a preferred embodiment is made of a ceramic material, thus causing the electric resistance of the refractory liner to be a multiple of the ohmic resistor R. This value assures a safe operation of the monitoring device. The crucible filled with melt is in an alternative embodiment a part of a conductor section. Particularly suited for this are electrically conducting electric or clay-graphite crucibles.

The respective conductor sections are longer in larger furnace systems, thus increasing their electric resistance to a considerable measure. It is advantageous in such cases to arrange several monitoring devices around the crucible filled with melt. Each individual monitoring device can also take on different tasks so that when melt runs out, for example, in connection with a special danger to personnel, the furnace is immediately switched off; in case of a run out without an immediate danger the furnace performance is at another area continuously controlled down.

The advantages achieved with the invention are in particular that in the event of a break of the cable there occurs a change of the display and thus a reliable and continuous monitoring of the function of the monitoring device is assured. In particular the system damages caused by a crack in the crucible are minimized and personnel is protected. Beyond already existing systems, the monitoring device functions in particular in furnaces with electric or clay-graphite crucibles since here the distinct dependency of the temperature of the resistance needed in other systems is unnecessary. Also additional devices such as, for example, contact flags, which are susceptible to trouble, are no longer needed. Melting furnaces can be monitored continuously and reliably for a break out of melt caused by a crack in the crucible and the safety of the system can be increased.

BRIEF DESCRIPTION OF THE DRAWINGS

Exemplary embodiments of the invention will be discussed in greater detail in connection with the drawings, in which.

DETAILED DESCRIPTION

Figure 1:
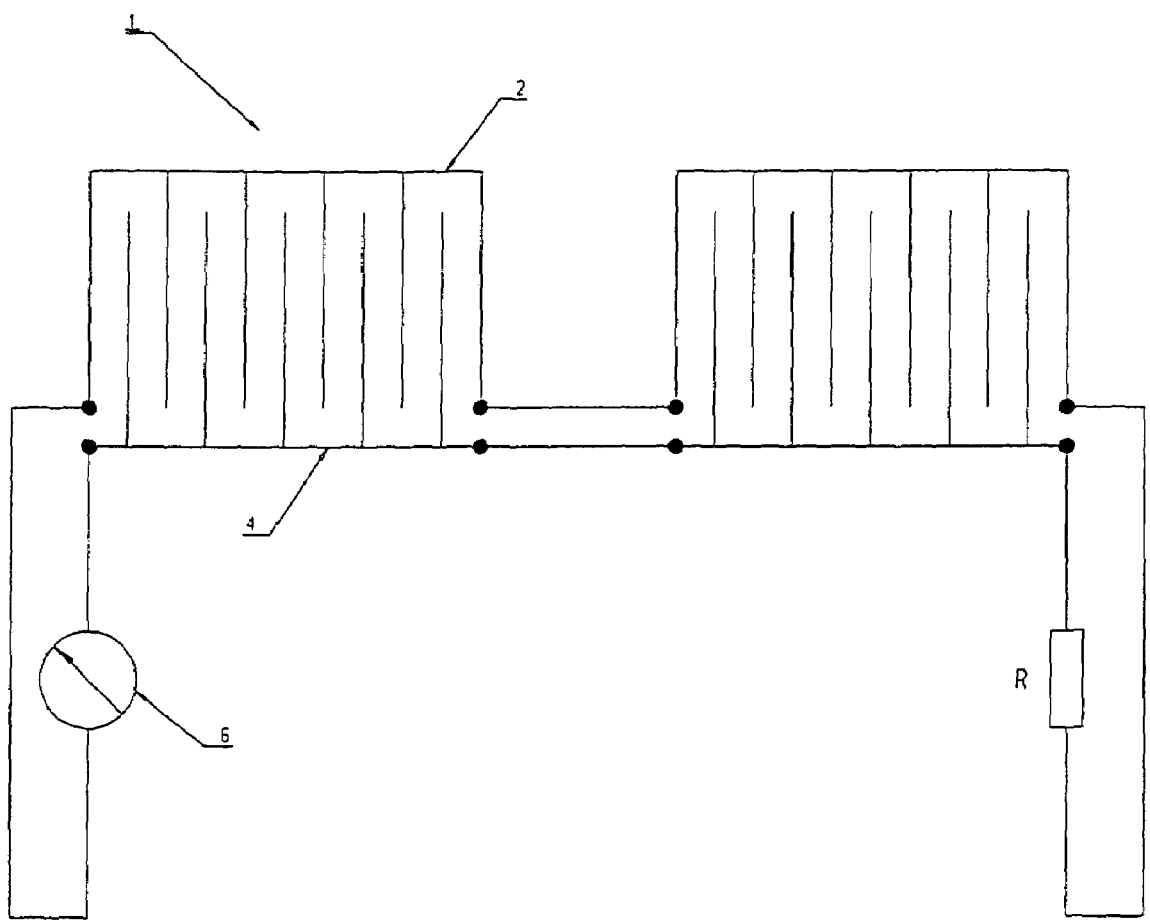
FIG. 1 illustrates a monitoring device with interleaved comb-like conductor sections.

Corresponding parts in all figures are identified with the same reference numerals.

The monitoring device 1 according to FIG. 1 includes a first conductor section 2 which is connected in series through an ohmic resistor R to a second conductor section 4, and forms a closed circuit having a measuring/displaying device 6. Both conductor sections have a comb-shaped design and are interleaved with one another so that the conducting paths are arranged directly adjacent, however, electrically isolated from one another. The comb-shaped area of the conductor sections represents the actual sensor region for the running out melt. The directly adjacent conductors are short-circuited as soon as metallic melt running out from a crucible contacts both. The ohmic resistor R, which is connected in series, lies in an area where it is not directly subjected to the high furnace temperature.

Figure 2:
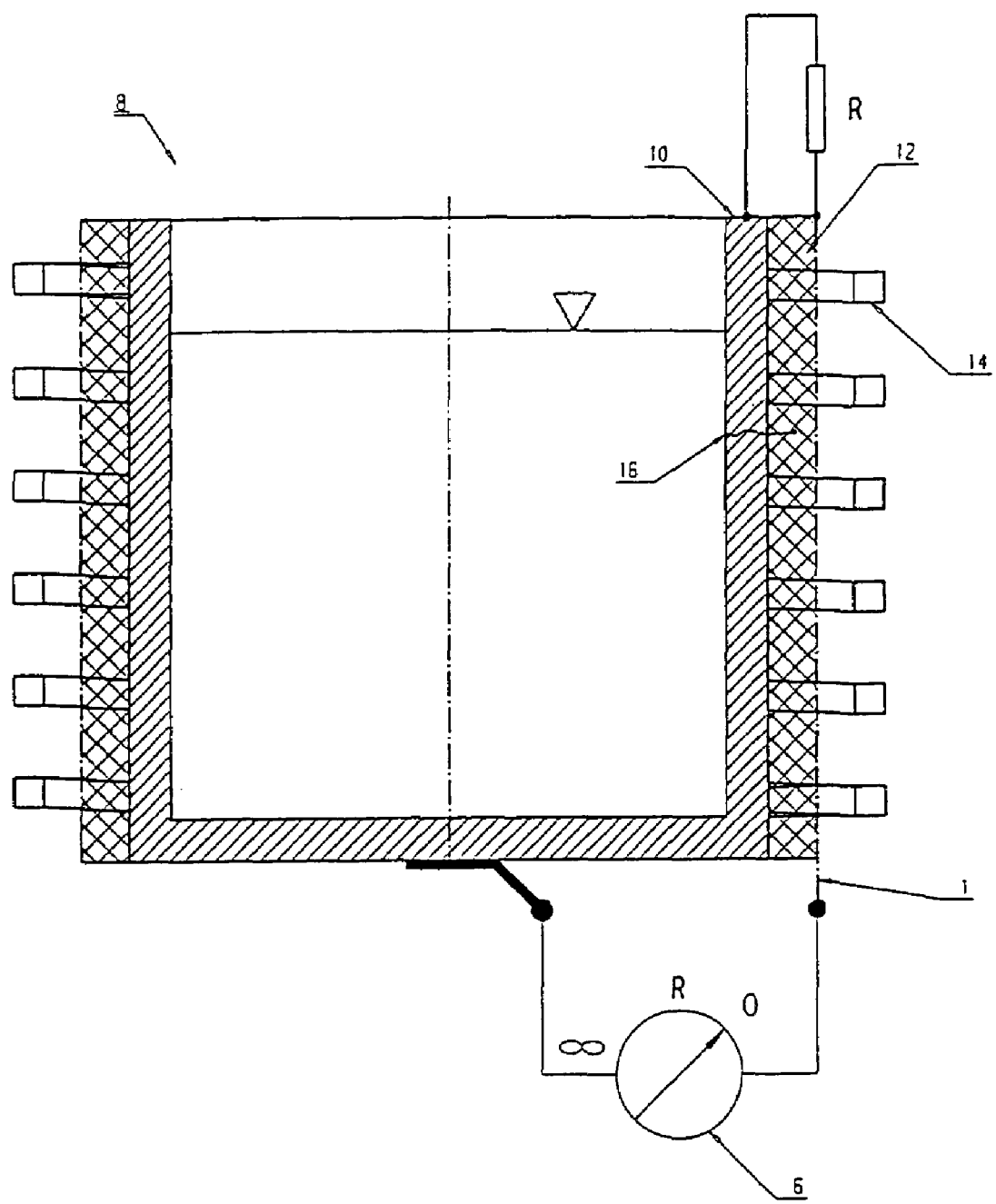
FIG. 2 illustrates a melting furnace with a monitoring device.

The exemplary embodiment according to FIG. 2 illustrates a melting furnace 8, designed as an induction furnace, with a monitoring device. The crucible 10 is surrounded by a refractory liner 12. A comb-shaped first conductor section 2 is mounted on the refractory liner 12 around the entire circumference of the crucible 10. The second conductor section 4 extends, starting from the electric resistor R, through the material of the crucible 10 and through the ground contact to the measuring/displaying device. The circuit is closed by the series connected ohmic resistor R, the crucible 10 with the ground contact, and the measuring/displaying device 6. The resistor R is dimensioned in such a manner that it is clearly smaller than the resistance value of the refractory liner 12, however, is also clearly larger than the resistor of the series connected conductor sections 2, 4. The resistor R lies advantageously between 1 and 5 kohms, a preferred value is 2 kohms. The monitoring device 1, in order to protect the coil 14, lies radially within the coil windings, which causes a melt tongue running out through a crack 16 to first short-circuit the conductor sections and thereafter to turn off the furnace performance.

Figure 3:
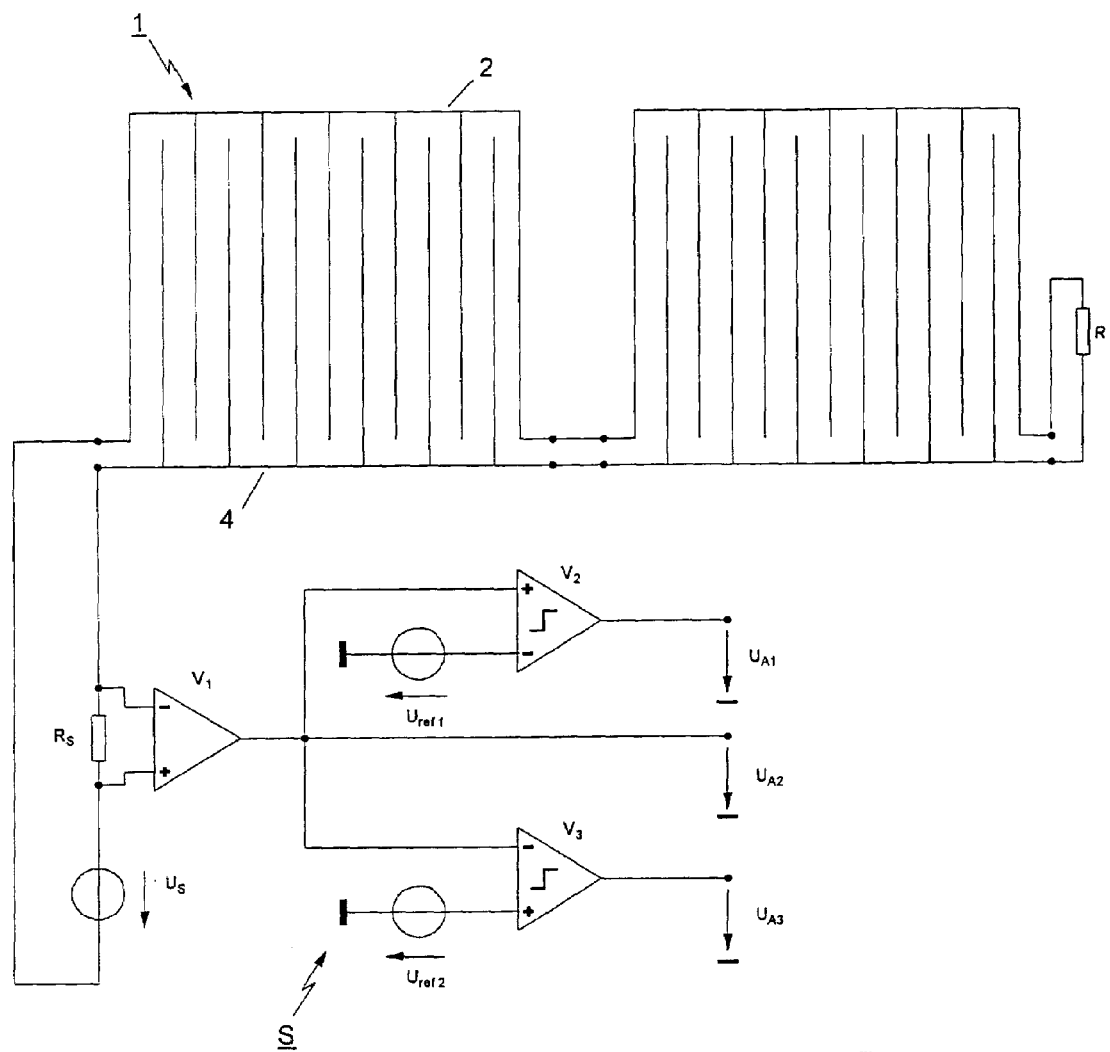
FIG. 3 illustrates a monitoring device with a display circuit.

The monitoring device 1 according to FIG. 3 includes comb-shaped conductor sections according to the exemplary embodiment of FIG. 1. In addition, the evaluating principle of the indicator circuit of the measuring/displaying device is illustrated in detail.

The operation of the circuit can be observed in the following list:

$U_{A1}$ changes during fracture of the pot from $U_{min}$ to $U_{max}$. This signal can be utilized to turn off the heating system.

$U_{A2}$ is a voltage proportional to the total resistance ($U_{min} \leq U_{A2} \leq U_{max}$). The signal can be utilized for checking and is adjusted through the amplification of the measuring amplifier $V_1$ in coordination with the supply voltage $V_S$ and the measuring resistor $R_S$ to approximately $U_{max}/2$.

$U_{A3}$ changes during system breakdown, for example, breakage of cable, from $U_{min}$ to $U_{max}$, and can be utilized to indicate the breakdown.

$U_{ref1}$ is used to adjust the switching threshold of the comparator $V_2$, and should clearly be larger than the nominal value of $U_{A2}$, however, smaller than $U_{max}$.

$U_{ref2}$ is used to adjust the switching threshold of the comparator $V_3$, and should clearly be smaller than the nominal value of $U_{A2}$, however, larger than $U_{min}$.

Further alternative embodiments, in particular a larger number of monitoring devices, are possible. These depend on the crucible size and the crucible geometry. It is, for example, advantageous to mount a further monitoring device at the bottom in crucibles with a flat bottom surface. The monitoring devices illustrated in FIGS. 1 to 3 can have besides the described flat comb or meandering configuration also parallel or focal point conductor sections, with which purposefully provided connection pieces or bores in the crucibles can be monitored.

What is claimed is:

1. A monitoring device for melting furnaces to facilitate the monitoring of a break out of melt, comprising a closed circuit of several electrically conductive sections with at least a partially conducting surface and a measuring/displaying device, wherein a first conductor section is series connected to an ohmic resistor R and a second conductor section, wherein the first conductor section is arranged directly adjacent, however, electrically isolatingly spaced from and with respect to the second conductor section, and wherein the ohmic resistor R is not subjected to the furnace temperature.

2. The monitoring device for melting furnaces according to claim 1, wherein the conductor sections are interleaved in a comb-like construction or are looped meanderingly around one another.

3. The monitoring device for melting furnaces according to claim 1, wherein the ohmic resistor R is larger by a factor of 100 to 1000 than a resistance value of the series connected conductor sections.

4. The monitoring device for melting furnaces according to claim 1, wherein the ohmic resistance value R=0.5 to 50 kohm.

5. The monitoring device for melting furnaces according to claim 1, wherein the ohmic resistance value R=1 to 5 kohm.

6. The monitoring device for melting furnaces according to claim 1, wherein the measuring/displaying device indicates during undisturbed normal operation essentially the magnitude of the ohmic resistor R, during breakdown due to a conductor break the resistance value of infinite, and during run out of melt the resistance value of zero corresponding to a short circuit.

7. The monitoring device for melting furnaces according to claim 6, wherein the resistance value indications of infinite or of zero are each coupled with an acoustic or optic display.

8. The monitoring device for melting furnaces according to claim 6, wherein the resistance value indication of zero is coupled with a device for turning off of the furnace.

9. A melting furnace with a monitoring device according to claim 1, wherein the conductor sections are arranged around a crucible filled with melt.

10. The melting furnace with a monitoring device according to claim 9, wherein the conductor sections are arranged holohedrally on the circumference of the crucible filled with melt.

11. The melting furnace with a monitoring device according to claim 9, wherein the conductor sections are arranged on a surface of a refractory liner which faces away from the crucible filled with melt.

12. The melting furnace with a monitoring device according to claim 11, wherein the refractory liner comprises a ceramic material.

13. The melting furnace with a monitoring device according to claim 9, wherein the crucible filled with melt forms a part of one of the conductor sections.

14. The melting furnace according to claim 9, wherein the monitoring device comprises one of several monitoring devices arranged around the crucible filled with melt to form a monitoring network.

15. The melting furnace with a monitoring device according to claim 9, including a refractory liner surrounding the crucible, wherein the ohmic resistor R has a resistance value that is clearly smaller than the resistance value of the refractory liner.

16. The monitoring device for melting furnaces according to claim 1, wherein the ohmic resistor ensures that the first and second conductor sections are otherwise electrically isolated from each other.

17. A monitoring device for melting furnaces to monitor a break out of melt, comprising:
   a measuring/displaying device;
   a first conductor section electrically connected to the measuring/displaying device;
   a second conductor section electrically isolated from the first conductor section and arranged adjacent to the first conductor section; and
   an ohmic resistor connecting the first conductor section and the second conductor section to form a closed series circuit, which ensures that the first and second adjacent conductor sections are electrically isolated from each other except for the current path of the ohmic resistor,
   wherein said device monitors the resistance of the series circuit to detect a short circuit between the first and second conductor sections resulting from a break out of melt therebetween.

18. The monitoring device for melting furnaces according to claim 17, wherein the ohmic resistor R is not directly subjected to the furnace temperature.

19. A furnace including the monitoring device according to claim 17, comprising:
   a crucible, wherein the monitoring device is arranged about the crucible; and
   a refractory liner surrounding the crucible, wherein the first conductor section is mounted on the refractory liner,
   wherein the ohmic resistor has a resistance value that is clearly smaller than the resistance value of the refractory liner.

* * * * *